United States Patent
Overes et al.

(10) Patent No.: US 6,648,896 B2
(45) Date of Patent: Nov. 18, 2003

(54) SPREADER APPARATUS FOR KNEE JOINTS

(75) Inventors: Tom Overes, Winterthur (CH); Bernhard Gyssler, Horgen (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 10/105,020

(22) Filed: Mar. 22, 2002

(65) Prior Publication Data

US 2002/0156480 A1 Oct. 24, 2002

(30) Foreign Application Priority Data

Mar. 29, 2001 (EP) .............................. 01810324

(51) Int. Cl.[7] .............................. A61B 17/56
(52) U.S. Cl. .............................. 606/90; 606/102
(58) Field of Search .............................. 606/86, 88, 90, 606/102, 105

(56) References Cited

U.S. PATENT DOCUMENTS

| | | |
|---|---|---|
| 3,200,501 A | 8/1965 | Keszler |
| 4,501,266 A | 2/1985 | McDaniel |
| 5,669,914 A | 9/1997 | Eckhoff |

FOREIGN PATENT DOCUMENTS

| | | |
|---|---|---|
| EP | 0809969 A2 | 12/1997 |

*Primary Examiner*—David O. Reip
(74) *Attorney, Agent, or Firm*—Townsend and Townsend and Crew, LLP

(57) ABSTRACT

Spreader apparatuses for knee joints are shown which have two parallel support plates (2, 3) which can be inserted between the femur condyles (4, 5) and the tibia (6) and which can be moved apart in connected form by an adjustment mechanism (10). The adjustment mechanism (10) has a housing (10) at which a stroke-extending tappet (17) is supported via an elastically resilient transmission member (7) in order to simultaneously make the effective spreading travel readable on a scale (8) at the housing (1) and the amount of the spreading force readable on a scale (9) at the housing (1).

11 Claims, 3 Drawing Sheets

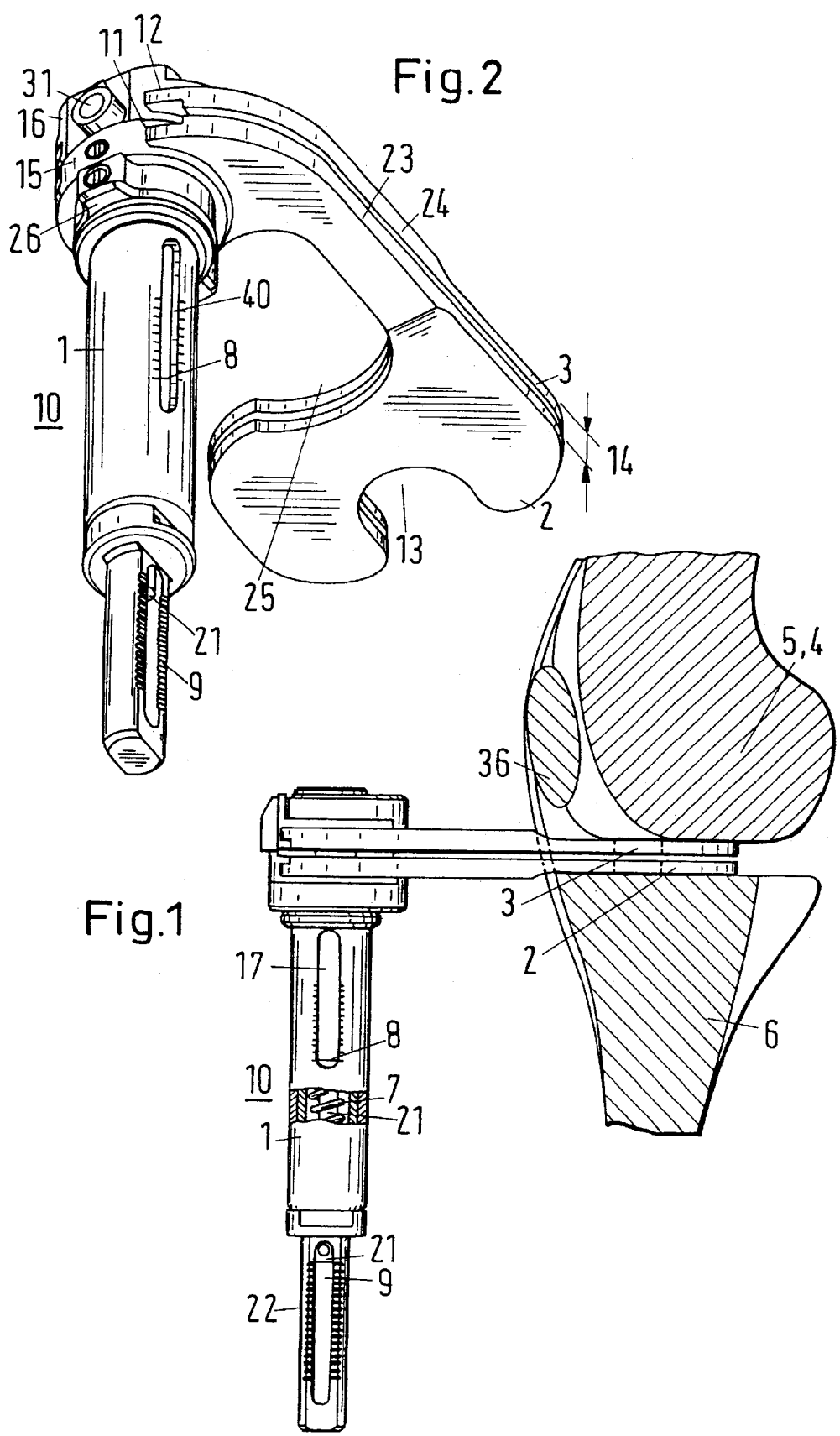

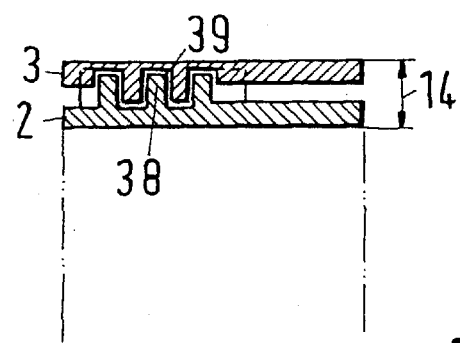
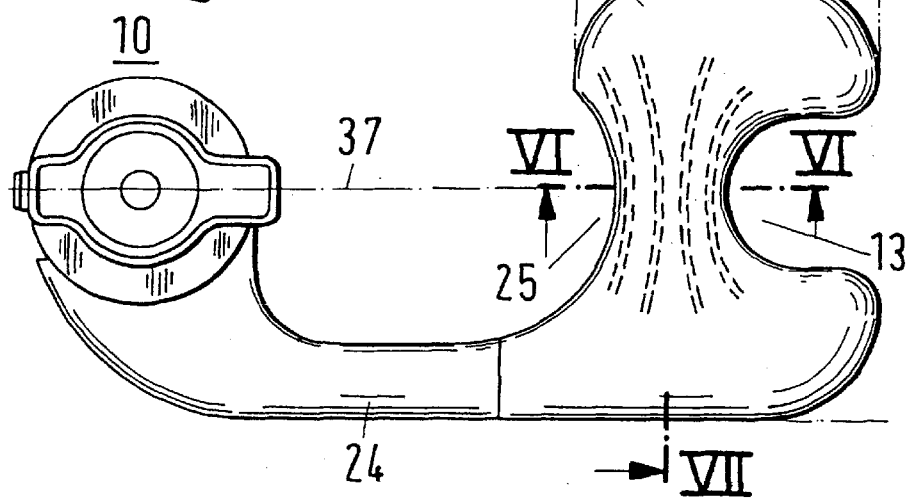
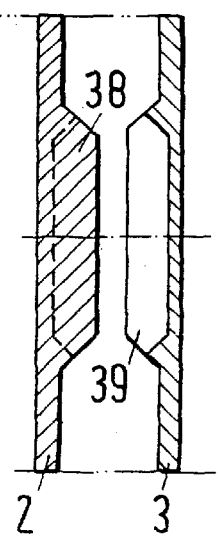

SPREADER APPARATUS FOR KNEE JOINTS

BACKGROUND OF THE INVENTION

The invention relates to a spreader device for knee joints comprising two parallel support plates which can be inserted between the femur condyles and the tibia and which can be moved apart by means of an adjustment mechanism which includes a housing.

Spreader apparatuses at joints serve for the spreading of an CD exposed joint in order to carry out certain surgical operations on the joint. For knee joints, such apparatuses have two parallel plates which are inserted between the tibia condyles and femur condyles and then moved apart with the aid of an adjustment mechanism.

A spreader apparatus of this kind is manufactured by Sulzer Orthopedics, Inc., 9900 Spectrum Drive, Austin Tex. 7871. The support plates are moved apart by means of a rack in whose teeth a spring pawl latches to secure the achieved spreading height. The vertical adjustment of the rack takes place via a gear which engages into the rack and can be driven via a crank. A disadvantage of this device lies in the fact that the operator does not have any information on the condition of the ligaments.

SUMMARY OF THE INVENTION

It is an object of the invention to provide remedial help in this direction with an improved spreader apparatus. This object is achieved with an adjustment mechanism that includes an elastically resilient transmission member to one of the support plates, in order to simultaneously make the effective spreading travel readable on a scale at the housing and the amount of the spreading force readable on a scale at the housing.

The advantage of the invention lies in the fact that the reaction forces of the ligaments can be read directly during spreading and can be compared to a likewise readable spreading height.

The support plates have a rear recess to protect cruciate ligaments which are still present. Since a further recess is provided at the front side of the support plates and since the connection to the adjustment mechanism takes place via a laterally receding web, an insertion of the support plates from the side is possible from the side without a web, for example from lateral, without the patella and the patella ligaments having to be removed from their natural position. The web is guided in an arc to the adjustment mechanism such that its feed axis lies in the sagittal central plane of the support plates. Since the support of a support plate, for example the upper support plate, takes place in this central plane in a hinge joint with a horizontal axis, the upper support plate can tilt away medially or laterally and display the current varus/valgus position between the femur and tibia to the operator. The operator thus has the possibility to examine the working of the ligaments under natural conditions. The support plates are connected to the adjustment mechanism via the webs by releasable plug connections. These plug connections are present a second time in mirror position at the central sagittal plane and are symmetrically designed so that the same support plates can be used for lateral or medial insertion. The releasable plug connection also allows support plates of different size to be used in pairs. Since the outer spacing of the support plates for the insertion of the support plates is limited and since bending deformations of the support plates of too large a kind are unwanted, it can be advantageous if the support plates have ribs and valleys in certain regions which mutually penetrate one another and give the individual support plate greater section modulus against bending.

The actual vertical adjustment of the spreading height takes place using a threaded screw, which is supported at the housing via an elastic spring, and moves a tappet which bears the upper support plate upwardly or downwardly. The thread has the advantage that a fine adjustment of the spreading height and a self-locking of the adjustment mechanism are given.

To take away as little room as possible in the operation area, the adjustment mechanism is designed such that it only projects a little beyond the upper support plate and is provided with a narrow tubular housing whose diameter has room twice in the dimensions of the support plate from lateral to medial. The tubular housing is extended by a rotary sleeve which includes an extension of the threaded screw with respect to rotation in form-locked manner. Contact surfaces are applied to the rotary sleeve so that additional space is only taken up by an applicable tool, for example a fork wrench, during the adjustment. The extension which projects out of the housing in dependence on the stressing of the spring between the threaded screw and the housing allows the spring force to be directly read off a scale of the rotary sleeve.

A further advantage of the design with exchangeable support plates lies in the fact that mono-condylar support plates can be used for only one joint half. However, in such a case, the hinge joint must be blocked or the connection webs must be guided to the adjustment mechanism such that the hinge axis comes to rest in the central sagittal plane of the mono-condylar support plates.

A further application provides for the fastening of cutting blocks to the support plates at predetermined positions in order to carry out resection incisions at bone parts in a position found to be optimum.

The invention is described below with reference to embodiments.

BRIEF DESCRIPTION OF THE DRAWINGS

FIG. 1 is a longitudinal section through a left knee joint with the side view of a spreader apparatus introduced from lateral, in schematic form;

FIG. 2 is a view, in schematic and enlarged form, obliquely from the bottom of a spreader apparatus having support plates in accordance with FIG. 1;

FIG. 5 is a plan view, in schematic form, of a spreader apparatus of FIG. 2;

FIG. 6 is a longitudinal section, in schematic form, through the support plates of FIG. 5; and FIG. 7 is a cross-section, in schematic form, through the support plates of FIG. 5.

DESCRIPTION OF THE PREFERRED EMBODIMENTS

Figure 3:
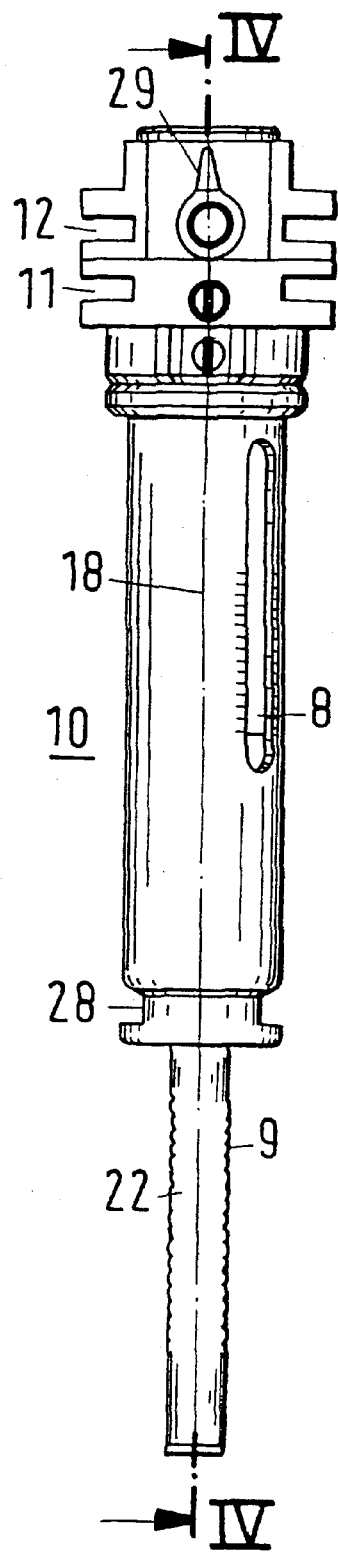
FIG. 3 is a front view, in schematic form, of a spreader apparatus in accordance with FIG. 2, without support plates.

Spreader apparatuses for knee joints are shown by the drawings which have two parallel support plates 2, 3 which can be inserted between the femur condyles 4, 5 and the tibia 6 and which can be moved apart in connected form by an adjustment mechanism 10. The adjustment mechanism 10 has a housing 1 at which a stroke-extending tappet 17 is supported via an elastically resilient transmission member 7 in order to simultaneously make the effective spreading travel readable on a scale 8 at the housing 1 and the amount of the spreading force readable on a scale 9 at the housing 1.

The same reference symbols are used for same functions in the following figures.

In the example of FIGS. 1 and 2, a pair of support plates 2, 3 is inserted behind the patella 36 between the femur condyles 4, 5 and the tibia 6 and connected to an adjustment mechanism 10 which has an upper scale 8 at its housing 1 which allows a view of a tappet 17 and its marking through a slit 40 in order to allow the effective tappet stroke to be read. A rotary sleeve 22 is rotatably supported at the housing at the lower side of the tubular housing 1. The rotary sleeve 22 is provided with a slit at whose edges a scale 9 for a spring force is attached. A setting screw 20, which engages into a threaded bore 19 (FIG. 4) of the tappet 17, drives apart the two support plates 2, 3. An elastically resilient transmission member 7 in the form of a helical spring, which supports the adjustment screw 20 against the housing 1, is pressed together in accordance with the resistance of the joint ligaments. Since the adjustment screw 20 has an extension 21 which extends into the rotary sleeve 22, the force applied to the helical spring can be read via the position of this extension 21. This extension is fitted in the rotary sleeve 22 in a form-locked, but longitudinally displaceable, manner in order to effect a rotation of the setting screw and thus a stroke adjustment via a rotation at the rotary sleeve.

The form of the bi-condylar support plates 2, 3, which have a front recess 25 and a rear recess 13, can be seen in FIG. 3. The lateral side of the support plates 2, 3 is continued in the form of a web 23, 24. The support plates 2, 3 have an insertion height 14 and contact grooves at the adjustment mechanism 10 in order to form a plug connection 11, 12. The receptions for the webs 23, 24 are formed for the upper web 24 by a fastening head 16, which is anchored to the tappet 17 via a hinge joint 31, and for the lower web 23 by a fastening head 15 which is a component of the housing 1.

Figure 4:
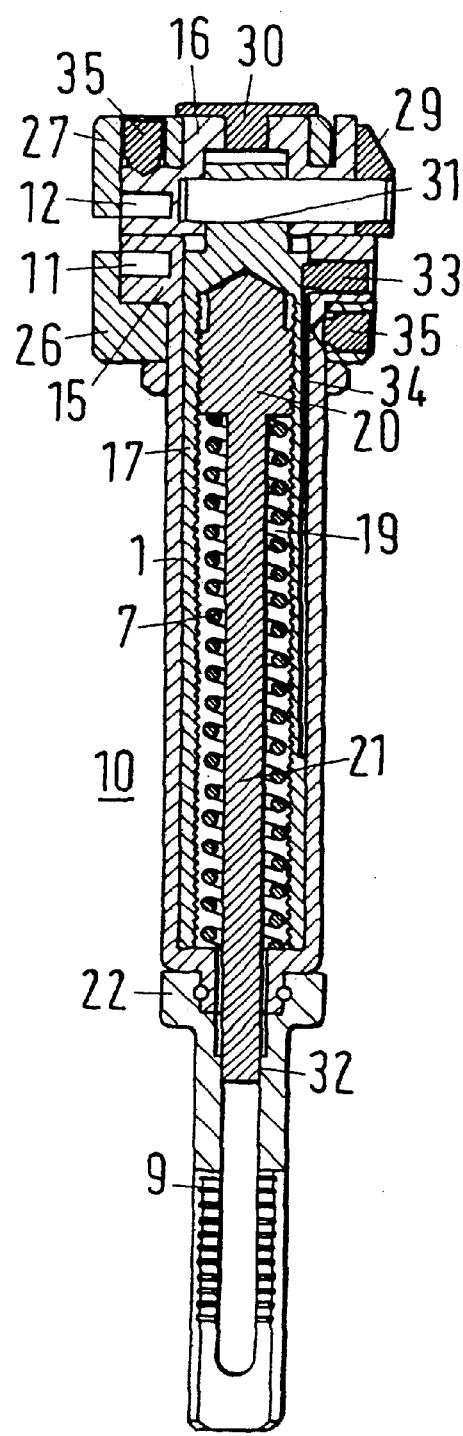
FIG. 4 is a longitudinal section, in schematic form, through the spreader apparatus of FIG. 3.

The purpose of the components of the adjustment mechanism can be seen in FIGS. 3 and 4. The upper fastening head can be pivoted around a hinge joint 31 with the tappet 17 extended and can tilt medially or laterally. The tilt movement can be read relative to a pointer 29 which is fastened to the hinge shaft. The inserted webs 23, 24 of the support plates 2, 3 are locked in place via rotary securing sleeves 26, 27, which each have a shoulder section projecting in the axial direction, and are blocked in turn by securing elements 35, for example by screws. The tappet 17, which is longitudinally displaceable in a bore of the housing 1, is guided with its elongate groove 34 through a bolt 33. The adjustment screw 20 sits in the threaded bore 19 of the tappet 17 and can be moved up and down in it by turning. It has an extension 21 which projects into the rotary sleeve 22 and is longitudinally displaceable there in a form-locked manner. The tappet 17 can be upwardly displaced relative to the setting screw 20, whereby the support plates move apart, by turning the rotary sleeve, for example at the contact surfaces 26, and by the form locking 32. As soon as the lower edge of the tappet 17 lifts off the housing 1, it only contacts the resilient transmission member 7, i.e. the helical spring. The helical spring is therefore always compressed in accordance with the spreading force when the tappet 17 is raised, with this spreading force being readable on the scale 9 of the rotary sleeve 22 in accordance with the position of the end of the extension 21. The longitudinal axis 18 of the adjustment mechanism 10 is in the central sagittal plane 37 (FIG. 6) of the support plates. The helical spring can be designed for a compression force of up to 300 Newtons. In practice, a range from 0 to 170 Newtons should be sufficient to inspect the working of the ligaments. The upper fastening head 16 is closed by a cover 30.

FIG. 6 shows a special embodiment of support plates 2, 3, which have ribs 38 and valleys 39 in the region of the central sagittal plane 37, which mutually penetrate one another in order to generate a greater section modulus despite the unchanged insertion height.

What is claimed is:

1. A spreader apparatus for knee joints comprising first and second parallel support plates which can be inserted between femur condyles and a tibia, an adjustment mechanism including a housing for moving the first and second plates apart, the adjustment mechanism including an elastically resilient transmission member to one of the support plates for simultaneously making the effective spreading movement readable on a first scale at the housing and the magnitude of the spreading force readable on a second scale at the housing, the housing being tubular and having a first fastening head for the first support plate and a tappet guided therein with a second fastening head for the second support plate, the tappet in the displacement axis being provided with a threaded bore and a setting screw rotatable disposed therein which is supported at the housing by the resilient transmission member in the form of a helical spring, an extension projecting out of the housing for rotating the setting screw, the projecting extension of the setting screw forming the second scale for the magnitude of the spreading force.

2. A spreader apparatus in accordance with claim 1, wherein the support plates are provided with releasable plug connections to the adjustment mechanism.

3. A spreader apparatus in accordance with claim 1, wherein the support plates have a lateral web to the adjustment mechanism allowing a spreading when the patella and the patella ligaments are present.

4. A spreader apparatus in accordance with claim 1, wherein the support plates have recesses for the cruciate ligaments.

5. A spreader apparatus in accordance with claim 1, wherein the adjustment mechanism has a hinge joint for one of the support plates for indicating a varus/valgus position in the spread position with an indicator.

6. A spreader apparatus in accordance with claim 1, wherein the support plates mutually penetrate one another in the starting position prior to spreading in order to obtain, with a pre-set insertion height over both plates, a greater section modulus with respect to bending for the individual first and second plates than the section modulus for plates with half the insertion height.

7. A spreader apparatus in accordance with claim 1, wherein the adjustment mechanism is self-locking in moving apart and moving together directions.

8. A spreader apparatus in accordance with claim 1, wherein the extension projects into a rotary sleeve supported at the housing allowing transmission of a torque to the extension by means of a form-fitted connection for different projecting amounts of the extension.

9. A spreader apparatus for knee joints comprising first and second parallel support plates which can be inserted between femur condyles and a tibia, an adjustment mechanism including a housing for moving the first and second plates apart, and an elastically resilient transmission member connected to one of the support plates for simultaneously displaying an effective spreading movement of the plates readable on a first scale of the housing and a magnitude of the spreading force applied to the plates readable on a second scale at the housing, the first and second support plates each having a lateral web extending in an arc to the adjustment mechanism for spreading the support plates apart so that their feed axis lies in a sagittal central plane of the support plates when the patella and patella ligaments of the knee joint are present.

10. A spreader apparatus in accordance with claim 9, wherein the adjustment mechanism comprises a tubular housing with a first fastening head for the first support plate and a tappet guided therein having a second fastening head for the second support plate.

11. A spreader apparatus in accordance with claim 10, wherein the tappet in the displacement axis includes a threaded bore and a setting screw rotatable in the threaded bore and supported at the housing, wherein the resilient transmission member comprises a helical spring, and wherein the setting screw can be rotated with an extension projecting out of the housing, the projecting extension of the setting screw forming a scale for the spreading force.

* * * * *